(12) United States Patent
Gale et al.

(10) Patent No.: US 7,297,758 B2
(45) Date of Patent: Nov. 20, 2007

(54) METHOD FOR EXTENDING SHELF-LIFE OF CONSTRUCTS OF SEMI-CRYSTALLIZABLE POLYMERS

(75) Inventors: David C. Gale, San Jos, CA (US); Syed Faiyaz Ahmed Hossainy, Fremont, CA (US); Bin Huang, Shoreview, MN (US); Klaus Kleine, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 76 days.

(21) Appl. No.: 11/195,974

(22) Filed: Aug. 2, 2005

(65) Prior Publication Data

US 2007/0032634 A1    Feb. 8, 2007

(51) Int. Cl.
    *C08F 6/00* (2006.01)
(52) U.S. Cl. .................. 528/480; 264/176.1; 264/219; 424/422; 424/426; 528/481; 606/108; 623/1.15
(58) Field of Classification Search ............. 264/176.1, 264/219; 424/422, 426; 528/480; 606/108; 623/1.15
    See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |

(Continued)

FOREIGN PATENT DOCUMENTS

DE    44 07 079    9/1994

(Continued)

OTHER PUBLICATIONS

Search Report for PCT/US2006/028309 filed Jul. 21, 2006, mailed Oct. 23, 2006 10 pgs.

(Continued)

*Primary Examiner*—Terressa Boykin
(74) *Attorney, Agent, or Firm*—Squire, Sanders & Dempsey LLC (57) ABSTRACT

This invention relates to a method of extending the shelf-life of constructs, in particular bioabsorbable stents, comprising semi-crystalline polymers by increasing the crystallinity of the polymers.

18 Claims, 5 Drawing Sheets

U.S. PATENT DOCUMENTS

| | | |
|---|---|---|
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 6,159,951 A | 12/2000 | Karpeisky et al. |

| Patent No. | Date | Inventor |
|---|---|---|
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236565 A1 | 12/2003 | Fifer |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Weber |
| 2004/0143317 A1 | 7/2004 | Stinson et al. |
| 2004/0167610 A1 | 8/2004 | Fleming, III |
| 2005/0004663 A1* | 1/2005 | Llanos et al. .............. 623/1.46 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 583 170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/09094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |

| WO | WO 2004/023985 | 3/2004 |

OTHER PUBLICATIONS

U.S. Appl. No. 10/317,435, filed Dec. 11, 2002, Hossainy et al.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23, No. 4, pp. 242-243 (1978).
Bull, *Parylene Coating for Medical Applications*, Medical Product Manufacturing News 18,1 pg. (Mar. 1993).
Casper et al. *Fiber-Reinforced Absorbable Composite for Orthopedic Surgery*, Polymeric Materials Science and Engineering, 53: pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastointestinal Anastomisis*, Journal of Investigative Surgery, vol. 9(6), pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules 2, pp. 430-441 (2001).
Hahn et al., *Biocompatibility of Glow-Discharge-Polymerized Films and Vacuum-Deposited Parylene*, J Applied Polymer Sci, 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Kelley et al., *Totally Resorbable High-Strength Composite Material*, Advances in Biomedical Polymers, 35, p. 75-85 (1987).
Kubies et al., *Microdomain Structure In polylactide-block-poly(ethylene oxide) copolymer films*, Biomaterials 21, pp. 529-536 (2000).
Kutryk et al., *Coronary Stenting: Current Perspectives*, a companion to the Handbook of Coronary Stents pp. 1-16 (1999).
Martin et al., *Enhancing the biological activity of immobilized osteopontin using a type-1 collagen affinity coating*, J. Biomed. Mater Res 70A, pp. 10-19 (2004).
Mauduit et al., *Hydrolytic degradation of films perpared from blends of high and low molecular weight poly(DL-lactic acid)s*, J. Biomed. Mater. Res. v. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., 1(4), pp. 438-448 (Jul./Aug. 1990).
Nichols et al., *Electrical Insulation of Implantable Devices by Composite Polymer Coatings*, ISA Transactions, 26(4), pp. 15-18 (1987).
Peuster et al., *A novel approach to temporary stenting: degradable cardiovascular stents produced from corrodible metal-results 6-18 months after implantation into New Zealand white rabbits*, Heart 86, pp. 563-569 (2001).
Pietrzak et al., *Bioabsorbable Fixation Devices: Status for the Craniomaxillofacial Surgeon*, J. Craniofaxial Surg. 2, pp. 92-96 (1997).
Pietrzak et al., *Bioresorbable implants—practical considerations*, Bon v. 19, No. 1, Supplement July 1996: 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, 79(2), pp. 445-457 (Feb. 1989).
Schmidt et al., *Long-Term Implants of Parylene-C Coated Microelectrodes*, Med & Biol Eng & Comp, 26(1), pp. 96-101 (Jan. 1988).
Spagnuolo et al., *Gas 1 is induced by VE-cadherin and vascular endothelial growth factor and inhibits endothelial cell apoptosis*, Blood 103, pp. 3005-3012 (2004).
Tamai et al., *Initial and 6-Month Results of Biodegradable Poly-I-Lactic Coronary Stents in Humans*, Circulation, pp. 399-404 (Jul. 25, 2000).
Tsuji et al., *Biodegradable Polymeric Stents*, Current Interventional Cardiology Reports 3, pp. 10-17 (2001).
Völkel et al., *Targeting of immunoliposomes to endothelial cells using a single -chain Fv fragment directed against human endoglin (CD105)*, Biochimica et Biophysica Acta 1663, pp. 158-166 (2004).
von Recum et al., *Degradation of polydispersed poly(L-lactic acid) to modulate lactic acid release*, Biomaterials 16, pp. 441-445 (1995).
Yau et al., Modern Size-Exclusion Liquid Chromatography, Wiley-Interscience Publication, IX-XV (1979).

\* cited by examiner

METHOD FOR EXTENDING SHELF-LIFE OF CONSTRUCTS OF SEMI-CRYSTALLIZABLE POLYMERS

FIELD

This invention relates to the fields of polymer chemistry and materials science.

BACKGROUND

Polymers are generally characterized by their bulk properties such as tensile strength, yield stress, modulus, hardness, stiffness, elongation, gas permeability, etc. It is these properties that manufacturers consult to determine whether a particular polymer would be suitable for a particular application. Thus, if a manufacturer requires a material that is hard and impact resistant for use in, say, motorcycle helmets, (s)he will select a type of polymer that exhibits those bulk properties whereas if the intended use requires flexibility, toughness and elongation, as might be case with expandable coronary stents, (s)he will choose a different type of polymer. The bulk properties of polymers can, however, change with time, a process known as aging. Aging can render a polymer no longer suitable for its originally intended purpose and possibly cause a construct comprising that polymer to fail in use with potentially disastrous consequences.

What is needed is a method of mitigating the aging process of polymers so as to extend the useful life, including the shelf-life of constructs composed thereof. The present invention provides such a method with regard to physical aging of semi-crystalline polymers.

SUMMARY

Thus, an aspect of this invention is a method of mitigating physical aging of semi-crystalline polymers, immiscible blends comprising one or more semi-crystalline polymer(s) or constructs of such polymer or polymer blends, comprising:

determining a glass transition temperature ($T_g$) of each polymer;

determining a melting temperature ($T_m$) of each polymer;

heating the polymer, immiscible blend of polymers or construct of such polymer or blend of polymers to a temperature between $T_g$ and $T_m$ of the polymer or one or more of the polymers of the immiscible blend of polymers;

holding the polymer, immiscible blend of polymers or construct of such polymer or blend of polymers at the temperature until one or more of the polymers independently is above about 25% crystalline and, removing the polymer, immiscible blend of polymers or construct of such polymer of blend of polymers from the source of heat.

In an aspect of this invention, the temperature is from about $T_g+0.05(T_m-T_g)$ to about $T_g+0.4(T_m-T_g)$.

In an aspect of this invention, the temperature is from about $T_g+0.17(T_m-T_g)$ to about $T_g+0.21(T_m-T_g)$.

In an aspect of this invention, the polymer, immiscible blend of polymers or construct of which polymer or polymer blend is held at the temperature until the polymer or at least one of the immiscible blend of polymers or at least one of the polymers comprising the construct is from about 40% to about 60% crystalline.

In an aspect of this invention, the polymer, immiscible blend of polymers or construct of which polymer or polymer blend is held at the temperature until the polymer or at least one of the immiscible blend of polymers or at least one of the polymers comprising the construct is from about 45% to about 55% crystalline.

In an aspect of this invention, the polymer or a polymer of the blend of polymers is poly(lactic acid).

In an aspect of this invention, the poly(lactic acid) is heated at from about 70° C. to about 100° C.

In an aspect of this invention, the poly(lactic acid) is heated at from about 75° C. to about 95° C.

In an aspect of this invention, the poly(lactic acid) is held at the selected temperature from about 5 minutes to about 15 minutes.

In an aspect of this invention, the poly(lactic acid) is held at the selected temperature from about 4 to about 7 minutes.

In an aspect of this invention, the poly(L-lactic acid) is from about 40% to about 45% crystalline after heating at a selected temperature for a selected time.

In an aspect of this invention, the construct is a medical device.

In an aspect of this invention, the medical device is an implantable medical device.

In an aspect of this invention, the implantable medical device is a stent.

In an aspect of this invention, the implantable medical device comprises a layer of poly(lactic acid).

In an aspect of this invention, the stent comprises a layer of poly(lactic acid).

In an aspect of this invention, crystallinity is determined by differential scanning calorimetry.

DETAILED DESCRIPTION

DEFINITIONS

As used herein, a "construct" refers to any useful article of manufacture made of a semi-crystalline polymer or immiscible blend of polymers of which at least one is semi-crystalline or any useful article of manufacture made of any material that is coated with a semi-crystalline polymer or immiscible blend of polymer blend of which at least one is semi-crystalline.

As used herein, "semi-crystalline" refers to a polymer that, at temperatures below its melting point, is capable of containing, and under most conditions does contain, both amorphous and crystalline domains. Amorphous domains are those in which polymer chains are situated in an essentially random orientation. Crystalline domains are those in which polymer chains adopt an ordered orientation with segments of separate chains or of the same chain becoming essentially parallel to one another to form structures known as lamellae. Lamellae begin from a point of nucleation, which normally is a speck of impurity in the liquid polymer and then grow outward from the nucleation point to form larger, essentially spherical crystalline structures know as crystallites. Unless otherwise expressly described otherwise, any reference to a polymer in the context of the method herein refers to a semi-crystalline polymer.

As used herein, an "immiscible blend" refers to a mixture of polymers in which the polymers form separate phases. If the blend constitutes more than one semi-crystalline polymer, the method herein may still be applied, most beneficially if a temperature can be found that is within the above parameters of this method for each, or as many as possible, of the semi-crystalline polymers in the blend. Furthermore, if a blend of polymers is being treated, it is presently preferred that at least one of the semi-crystalline polymer(s) to which the method herein is applied comprises the continuous phase of the blend.

As used herein, "mitigating" means to eliminate, reduce the effects of, eliminate the recurrence of or increase the time to recurrence of physical aging due to densification in the amorphous regions of a semi-crystalline polymer.

As used herein, "shelf-life" refers to the length of time a construct can be stored at room temperature before sufficient physical aging of the polymers of which it is comprised takes place to render the construct unfit for use for its intended purpose.

Discussion

Polymers age by physical, chemical and/or electrical processes. Chemical aging results from exposure of a polymer to such external factors as air (oxygen), moisture, solvents, radiation, heat and light. Electrical aging results from voltage-induced stress that occurs at voltages usually in excess of about 3 kilovolts. Physical aging, which is the primary focus of this invention, results from residual and applied stresses. As used herein, a "residual stress" includes, without limitation, stress in a bulk polymer that is in a non-equilibrium thermodynamic state.

Physical aging of semi-crystalline polymers that have glass transition temperatures ($T_g$) above their normal storage temperature, which, for the purposes of this invention is room temperature, i.e., from about 15° C. to about 35° C., occurs primarily through the phenomenon known as densification.

Densification occurs when a semi-crystalline polymer is cooled at a non-equilibrium rate from a temperature above its $T_g$ to a temperature below its $T_g$. Such is in fact normally what will occur in most industrial settings in that equilibrium cooling is very slow and would be considered economically impractical. The non-equilibrium cooling rate results in the randomly oriented polymer chains of the amorphous domains being trapped at non-optimal separation distances in the glassy state that forms when the temperature goes below $T_g$. The chains then attempt to achieve optimal separation by coordinated localized chain motion. As the average distance between chains decreases, a decrease in polymer free volume occurs, that is, that space within the bulk polymer not physically inhabited by portions of polymer chains is reduced. The loss of free volume results in an increase in polymer density per unit volume, thus the term "densification." As the polymer densifies, non-covalent chain-chain molecular interactions increase. Although the interactions do not result in chain ordering, that is, the formation of lamellae and crystallites, which would constitute crystallization, the effect on the bulk properties of the polymer is similar to that obtained when crystallization occurs: the modulus of the polymer increases and concomitantly the polymer becomes more brittle. Thus, densification of a polymer initially selected for toughness and elasticity could result in failure of a construct made of or coated with the polymer when the polymer ages or densifies and becomes brittle. Densification can occur relatively rapidly in reference to the desired shelf-life of constructs comprising semi-crystalline polymers such that control of densification can result in significantly extending the shelf-life of such constructs.

Figure 1A:
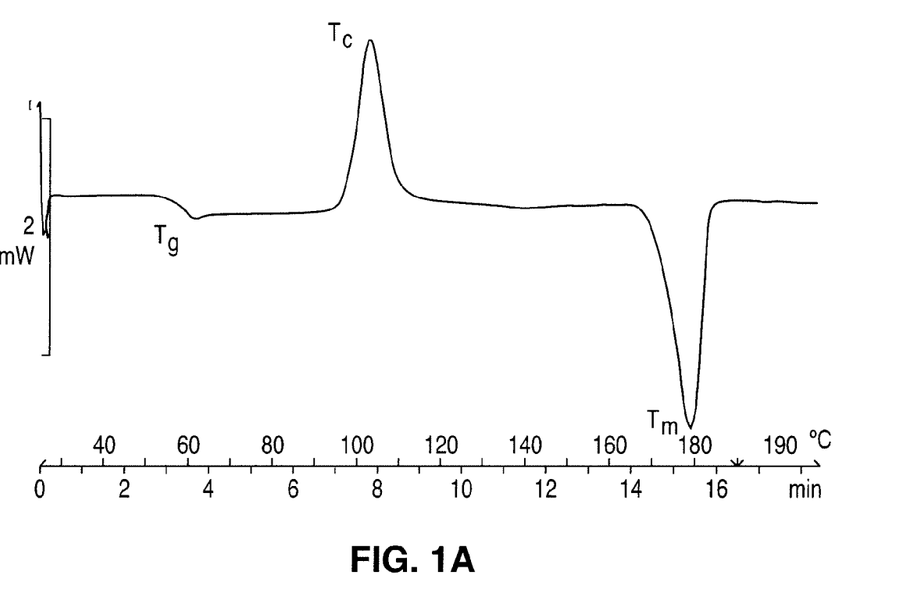
FIG. 1A is a generic representative DSC thermogram showing the three normal thermal transitions usually seen in thermograms of un-aged semi-crystalline polymers.

Densification of a polymer can be observed and qualitatively tracked by differential scanning calorimetry (DSC). Briefly, DSC measures the thermal transitions that a polymer goes through on heating. For a semi-crystalline polymer, there are normally three such thermal transitions, the glass transition, $T_g$, the latent heat of crystallization, $T_c$, and melting, $T_m$. A typical DSC thermogram, as the resulting plot called, is shown in FIG. 1A with $T_g$, $T_c$ and $T_m$ labeled. One of the fundamental uses of DSC is to determine the percent crystallinity in a semi-crystalline polymer. In brief, this is accomplished by first calculating the area under the $T_m$ peak. Melting is an endothermic process, that is, heat must be added to the system to melt the crystalline regions of the polymer. The area is then divided by the rate of heating to give the number of joules per gram of sample that was needed to melt all crystalline domains in the sample when the sample reached its melting point. Multiplying joules per gram by the size of the sample in grams gives the total amount of heat that was required to melt those crystalline regions, $H_t$. The exercise is repeated for the $T_c$ peak to give $H_c$, the amount of heat given off by the system as crystallization was taking place, the latent heat of crystallization being exothermic. ($H_t$–$H_c$) gives the amount of heat, $H_m$, that was required to melt the crystalline domains that existed before the polymer was heated above $T_g$. The specific heat of melting, $H_{sm}$, of the polymer may generally be looked up in the literature since many are known in the art but, if not, it may be empirically obtained by repeating the above experiment using exactly one gram of polymer. Dividing $H_m$ by $H_{sm}$ provides the number of grams of the sample that were crystalline before the polymer was heated above $T_g$. ($H_m/H_{sm}$) X 100 gives the percent crystallinity of the polymer when it was below $T_g$.

Figure 1B:
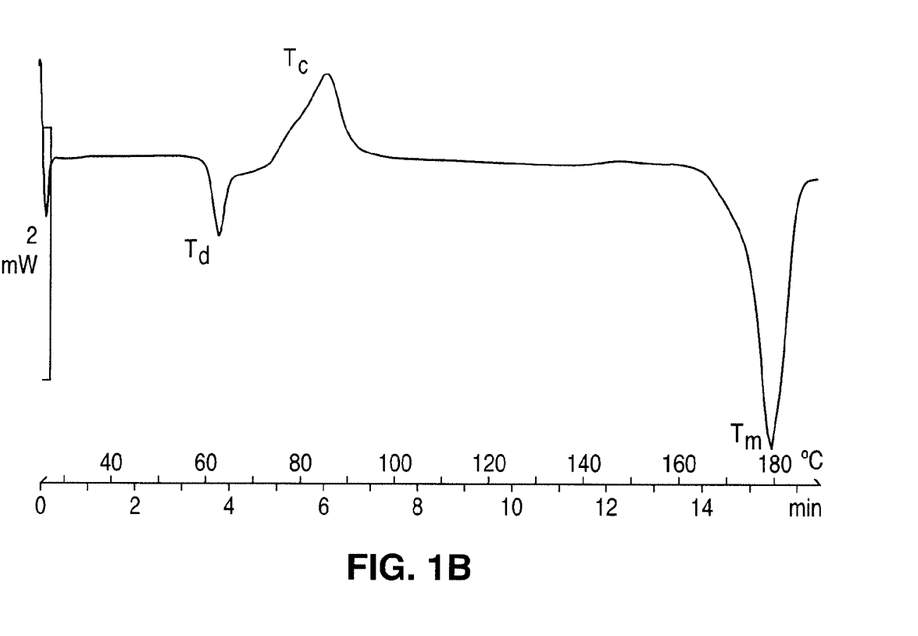
FIG. 1B is a generic representative DSC thermogram showing the peak indicating aging of a semicrystalline polymer.

FIG. 1B shows a generic thermogram as it would appear for an aged semicrystalline polymer. In the region of $T_g$, as opposed to a smooth exothermic transition to higher heat capacity, a distinct peak, indicated by $T_d$, for T-sub-densification, is observed. It is this peak that is presently thought to represent aging of the polymer. As will be seen in the examples that follow, this is supported by the fact that the peak disappears when the polymer sample is subjected to a second DSC run after the completion of the first, that is after the polymer has been melted, become completely. amorphous and, as a result, lost any characteristics that would be attributable to its temporal history. That is, the disappearance of the $T_d$ peak suggests that this peak is the result of the polymers temporal history and therefore is reasonably attributable to aging.

Figure 2:
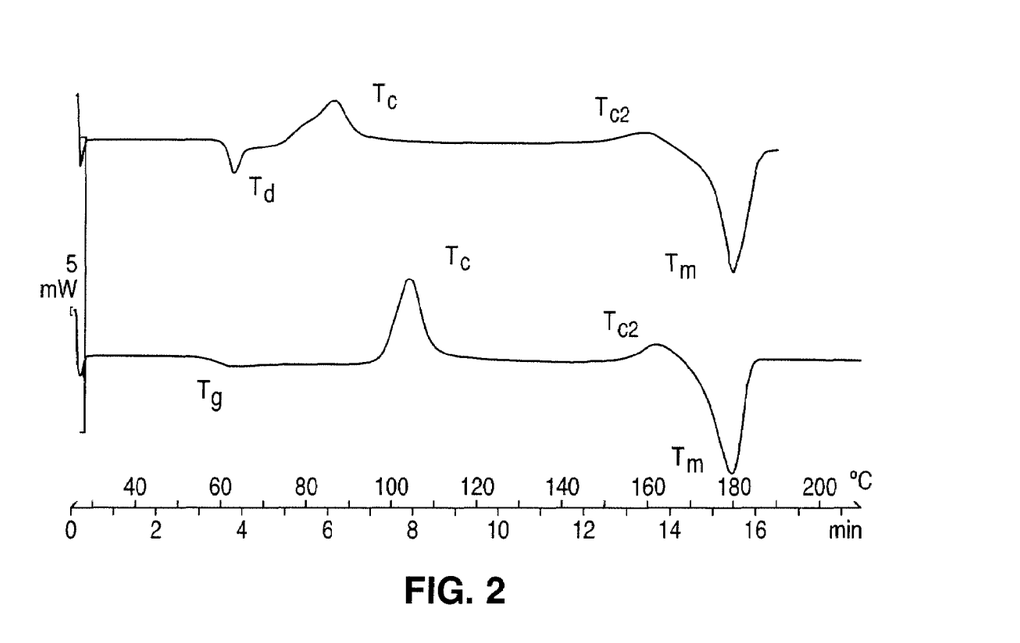
FIG. 2 is a DSC thermogram of a sample of PLA that has been stored at room temperature for approximately three months.

FIG. 2 is a DSC thermogram of a sample of semi-crystalline poly(lactic acid) (PLA) which had been stored at room temperature for three months. The thermogram reveals five rather than three thermal transitions. $T_g$, $T_c$ and $T_m$, as described with regard to FIG. 1, are labeled. $T_{c2}$, the exact origin of which has not been firmly established, is presently thought to be due to rearrangement of imperfections in crystalline domains to more regular ordered structures created during initial crystallization at $T_c$. More interesting is the peak, $T_d$, seen in the vicinity of $T_g$ because it is this peak which is presently thought to be due to densification of the polymer in the sample. To examine whether such is the case, a second DSC was run on the sample immediately after the first. Once the sample reached $T_m$ during the first DSC run, all thermal history of the sample was eliminated. That is, the sample was returned to its liquid amorphous state in which no crystallinity nor any densification exists. If in fact $T_d$ were related to densification or physical aging, then it ought not be evident in the rerun thermogram of the polymer. That is exactly what is observed. In the thermogram on the freshly cooled sample was obtained, $T_g$, $T_c$, $T_{c2}$ and $T_m$ were all still apparent in the plot but $T_d$ has disappeared.

Additional DSCs exploring $T_d$ and the effects of various physical characteristics of the polymer thereon, namely draw ratio, radial expansion and initial degree of crystallinity on $T_d$ can be seen in FIGS. 3-8.

Figure 3:
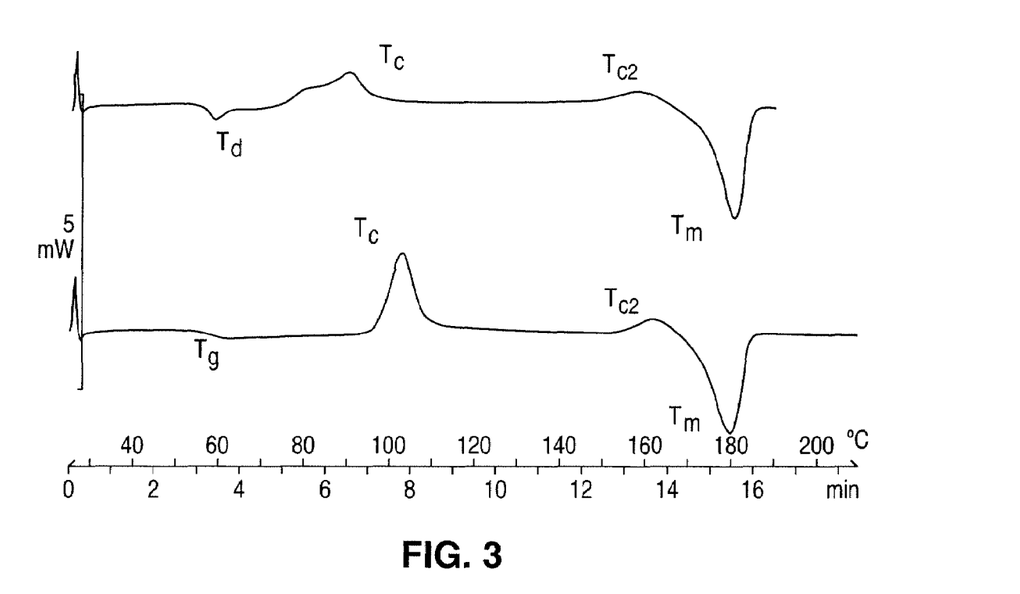
FIG. 3 is a DCS thermogram of the above sample after storage at room temperature for 14 days.

In FIG. 3, a DSC of the same sample used to create the thermogram of FIG. 2 is shown, except that the PLA had been aged for 14 days rather than three months. As can be seen, $T_d$ is evident but the peak is smaller than that in FIG. 2. This suggests that the sample of FIG. 2 had undergone more densification and thus more aging than the sample of FIG. 3, which is exactly the case, further solidifying the assignment of $T_d$ to physical aging of the sample.

Figure 4:
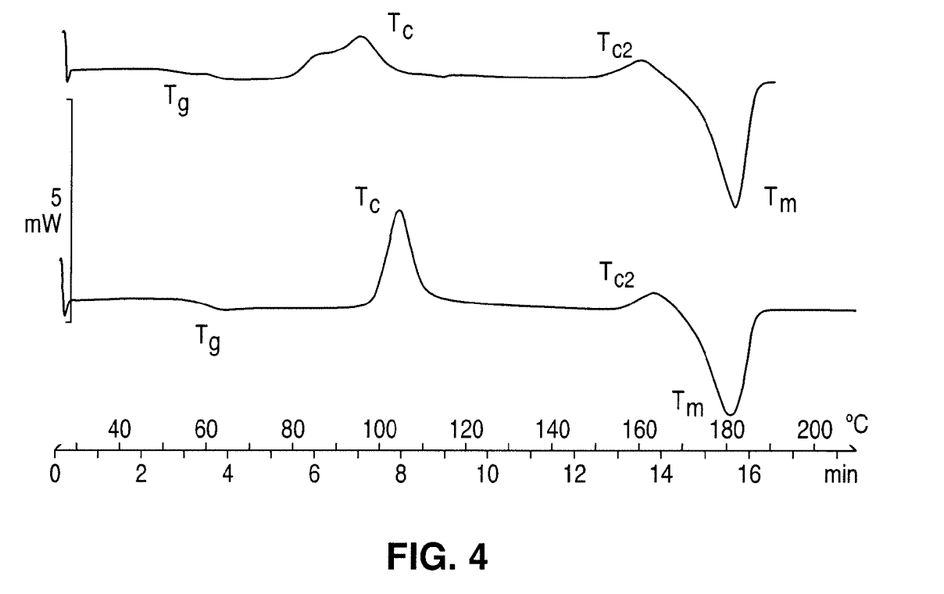
FIG. 4 is a DSC thermogram of the same sample of FIGS. 2 and 3 except that the sample was not aged at all before the run.

FIG. 4 is a DSC of the same sample used to obtain the thermograms of FIGS. 2 and 3, except that it was run immediately after cooling the PLA from the melt, that is, with no aging at all. As can be seen, there is no $T_d$ peak, further confirming that this peak is indeed indicative of densification and physical aging.

Figure 5:
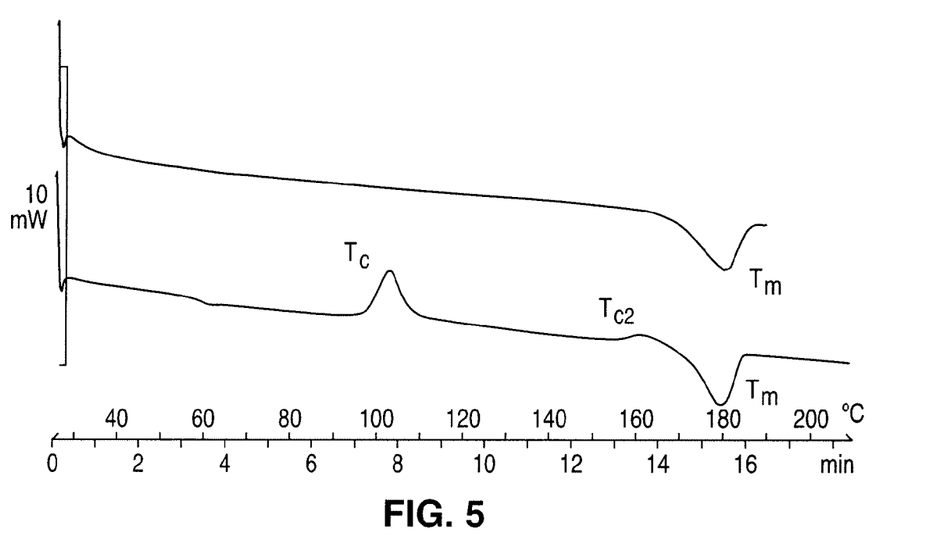
FIG. 5 is a DSC thermogram of a sample of PLA tubing, 46% crystallinity, 3.4 draw ratio after one month a room temperature.

FIG. 5 shows a thermogram of a PLA sample that had been subject to a high draw ratio (3.4) and thereby exhibited a high degree of crystallinity (46%). After one month at room temperature, the initial thermogram and the immediate rerun thermogram show $T_g$ and $T_m$ but neither exhibits any $T_d$. The absence of $T_c$ in the initial thermogram may be attributed to the fact that the high draw ratio induced maximum crystallinity in the sample so that no further crystallization occurred between $T_g$ and $T_m$. The appearance of $T_{c2}$ in the rerun thermogram suggests crystalline defects were introduced during the second run through $T_c$.

Figure 6:
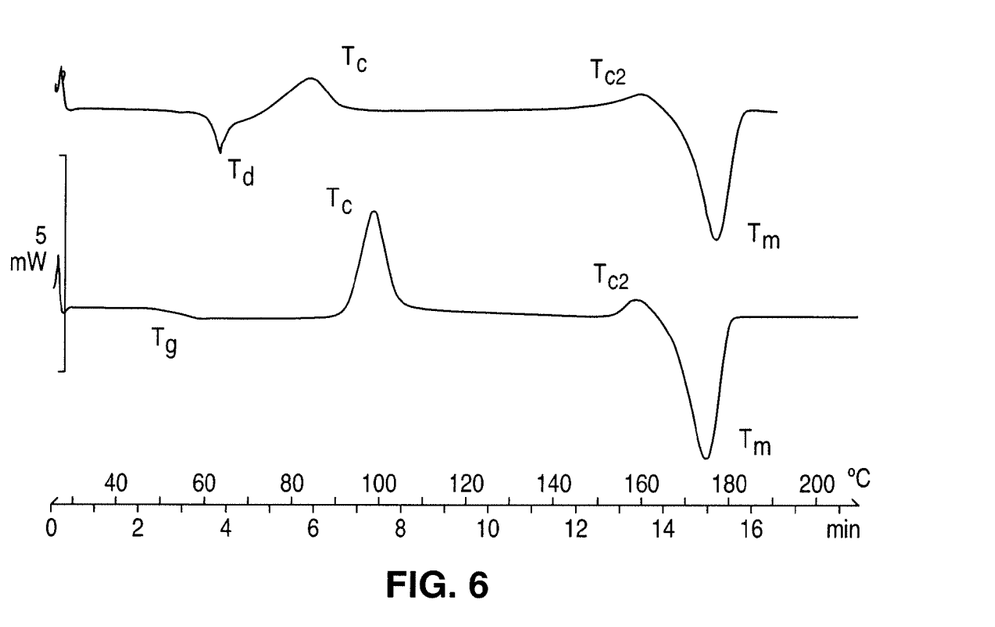
FIG. 6 is a DCS thermogram of a 25% crystalline PLA stent after two weeks at room temperature.

FIG. 6 shows a thermogram run on a sample of a two-week old stent fabricated from PLA which had undergone a low draw ratio, 1.0, and had a relatively low degree of crystallization, 25%. As can be seen, the upper plot reveals a $T_g$, a $T_d$, a $T_c$, a $T_{c2}$ and a $T_m$ while the second rerun plot shows each of these except for $T_d$. Thus, the DSC shows that the sample had undergone considerable physical aging in just two weeks.

Figure 7:
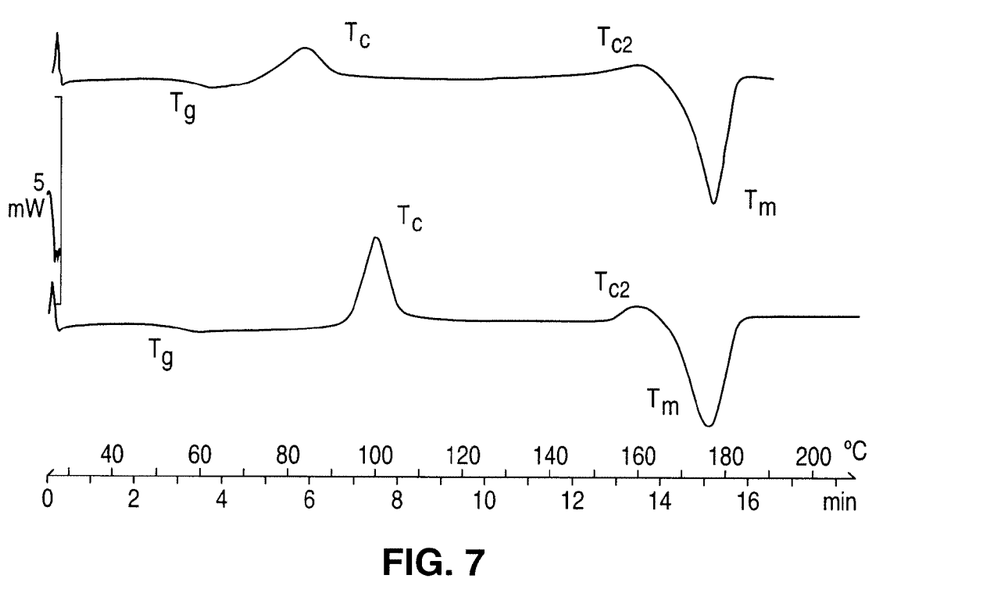
FIG. 7 is a DSC thermogram of the stent of FIG. 6 after it had been heated to 60° C. for approximately one hour.
Figure 8:
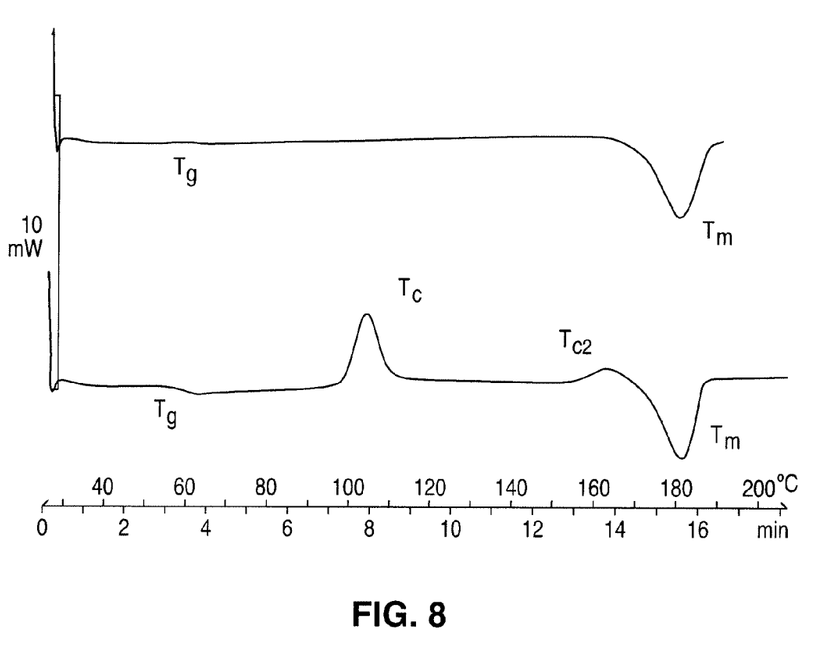
FIG. 8 is a DSC thermogram of a 50% crystalline PLA sample after storage at room temperature for approximately one month.

FIG. 7 show a thermogram of a sample of the same stent used to generate the plot in FIG. 6. Here, the sample had been heated to approximately 60° C. for about one hour prior to running the DSC. $T_d$ is completely absent from the plot.

Thus, it appears that physical aging due to densification can be reversed by heating the polymer to a temperature between $T_g$ (about 58° C. for PLA) and $T_m$; i.e., it is not necessary to completely melt the polymer.

Since a polymer need not be melted to reverse densification, physical aging in constructs made of or coated with a semi-crystalline polymer should be reversible without damaging the constructs or coating, thus providing a means of extending the useful life, including the shelf-life, of such constructs. The question becomes, is there a way to control the rate of re-densification such that it would not be necessary to subject a construct to repeated heating and cooling which could exacerbate chemical aging and speed the demise of the construct? The answer lies in the fact that the rate of densification is related to the degree of crystallization.

As pointed out previously, densification results from localized segmental movement of polymer chains in amorphous region of a polymer at temperatures below $T_g$ as the chains attempt to achieve thermodynamic equilibrium with regard to chain separation distance. This is a slow process since in the glassy state below $T_g$ very little thermal energy is available to effect chain motion. If the polymer chains are further involved in inter- or inner-chain crystalline structures, that is, lamellae and spherulites, that are dispersible only upon melting, the lengths of chain in the amorphous domains that are still capable of movement are reduced and the ability of the chains to densify is correspondingly lessened. That such is the case can be seen in FIG. 8 where a thermogram of a sample of a 50% crystalline PLA sample that was stored for approximately one month is shown. As can be seen, the first and second DSC runs appear substantially identical in the $T_g$ region; i.e., there is no evidence of any densification as indicated by the absence of a $T_d$. Thus, it would be expected that increasing the degree of crystallinity of a polymer should reduce or even eliminate physical aging. However, crystallization itself is an undesirable characteristic of polymers that are used to fabricate constructs that rely on toughness, durability, flexibility and elongation of the polymer for their utility because crystallinity confers increased modulus and brittleness on a polymer. Thus, it would be desirable to use polymers that are more crystalline in order to mitigate densification, i.e., physical aging, but that avoid the changes in bulk properties that accompany increased crystallinity. The answer to this conundrum lies in the thermodynamics of crystallization.

As the temperature of a semi-crystalline polymer is raised from $T_g$ the rate of crystallization increases logarithmically until the temperature reaches $T_m$ at which point the crystal domains melt and the polymer chains resume a amorphous, completely random orientation. During the temperature run, several processes occur. Polymer crystallization begins with nucleation, the formation of small crystalline domains around specks of impurities in the sea of amorphous liquid polymer. Nucleation occurs most efficiently at temperatures near $T_g$. Crystal growth, the formation of lamellae and crystallites, on the other hand, occurs most rapidly at temperatures near $T_m$. Thus, at various temperatures between $T_g$ and $T_m$ it should be possible to control the relationship between degree of nucleation and associated crystal growth with the greatest amount of nucleation coupled with the least amount of crystal growth occurring at temperatures above but near $T_g$. The formation of large number of small crystalline domains should have the effect of drastically restricting polymer chain motion in the remaining amorphous domains of a polymer while not substantially affecting the desirable bulk properties of the polymer. Furthermore, the restricted motion of the polymer chains should reduce, even eliminate, densification and, thus, physical aging of the polymer.

It has been found that heating a semi-crystalline polymer to a temperature that is above $T_g$ by about 5% to about 40%, preferably from about 17% to about 21% of the difference between $T_g$ and $T_m$ for a relatively brief period of time, typically from about 1 minute to about 20 minutes, preferably about 3 minutes to about 10 minutes, followed by cooling the polymer to room temperature which may include forced cooling or simply removing the polymer from the source of heat and allowing it to cool naturally under ambient conditions to room temperature, will yield a polymer that has a relatively high degree of crystallinity, preferably from about 40% to about 60%, more preferably at present from about 45% to about 55% wherein the crystallinity is due primarily to a large number of small crystalline regions rather than fewer but larger crystallite-containing regions. The result is a polymer in which the propensity to densify is drastically curtailed if not virtually eliminated but that still retains the bulk properties required of it for its particular application.

The above temperature can be calculated using the equation $T=T_g+X(T_m-T_g)$ where X is about 0.05 to about 0.4 and more preferably, from about 0.17 to about 0.21. For example, without limitation, for PLA having a $T_g$ of approximately 60° C. and a $T_m$ of approximately 180° C., the temperature T to which it would be heated is from 60+0.05 (180–60) to 60+0.4(180–60) or from 66° C. to about 108° C., preferably from 60+0.17(180–60) to 60+0.21(180–60) or from approximately 80° C. to approximately 85° C.

The above process can be applied to a semi-crystalline polymer or immiscible blend in which at least one polymer is semi-crystalline prior to the polymer or blend being used in a construct. Thus, for example without limitation, extruded PLA can be treated using the method herein, cooled and laser-cut into balloon expandable stents.

In addition to treating a semi-crystalline polymer or polymer blend prior to fabrication of a construct, the method herein may be applied to fully formed constructs. The only caveat is that the construct cannot contain any substance, such as a drug, that might be detrimentally affected at the requisite temperatures of this method. In this manner physical aging of existing constructs can be reversed, with the resulting construct being expected to have a much longer useful lifespan, including a substantially extended shelf-life, due to the resistance to re-aging imparted by the method herein.

While the method of this invention can be applied to any semi-crystalline polymer or to any construct of such polymer or blend of polymers, it is presently a preferred embodiment of this invention that it be applied to polymers that are used for the fabrication of implantable medical devices or are coated onto such implantable medical devices. Implantable medical devices tend to be expensive and their required performance characteristics stringent. Physical aging can render such devices unusable in a relatively short period of time resulting in a potentially huge expense. Thus, it is anticipated that the method herein will find particular application both as a treatment for polymers used to make or coat such devices and as a treatment for devices already in existence and that have been stored for a period of time waiting to be used.

An implantable medical device refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, self-expandable stents, balloon-expandable stents, stent-grafts, grafts, artificial heart valves and cerebrospinal fluid shunts. In particular, the method herein should be useful in the fabrication and maintenance of stents for the purpose of extending their shelf-lives.

The primary use of a stent is to maintain the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, re-stenosis and vulnerable plaque Vulnerable plaque (VP) is a type of fatty build-up in an artery thought to be caused by inflammation. The VP is covered by a thin fibrous cap that can rupture leading to blood clot formation and the stent acts as a shield against such rupture. A stent may, however, also be used for localized delivery of a bioactive agent to a selected treatment site in a patient's body.

The stent may be self-expandable or balloon expandable. Any type of stent currently known to, or as such may become known to, those skilled in the art may be fabricated of or coated with a semi-crystalline polymer or blend of polymers that has been subjected to the method herein. In the alternative, a stent already so fabricated or coated may be subjected to the method herein to eliminate any densification that has taken place and inhibit or eliminate its recurrence.

For implantable medical devices, in particular at present for stents, that have been or are to be coated with a semi-crystalline polymer or immiscible blend of polymers of which as least one is semi-crystalline, the device may be made of virtually any material that is amenable to such coating. Examples, without limitation of which materials include biocompatible metals or alloys such as, but not limited to, cobalt chromium alloy (ELGILOY), 316L stainless steel, high nitrogen stainless steel, e.g., BIODUR 108, nickel-titanium alloy (NITINOL), tantalum, platinum, platinum-iridium alloy, gold and combinations thereof.

Alternatively, the implantable medical device or stent may be made of one or more biocompatible, relatively non-biodegradable polymers including, but not limited to, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins. Any of these polymers that is semi-crystalline can, of course, be subjected to and expected to benefit from the method herein with regard to their physical aging by densification. It is presently preferred that the method of this invention be applied to stents made of bioabsorbable semi-crystalline polymer or polymers so as to extend their shelf-lives.

As noted above, a stent may be used for the localized deliver of bioactive agent(s). As used herein, a bioactive agent refers any substance that is of medical or veterinary therapeutic, prophylactic or diagnostic utility. Therapeutic use refers to a bioactive agent that, when administered to a patient, will cure, or at least relieve to some extent one or more symptoms of, a disease or disorder. Prophylactic use refers to a bioactive agent that, when administered to a patient either prevents the occurrence of a disease or disorder or, if administered subsequent to a therapeutic agent, prevents or retards the recurrence of the disease or disorder. For the purposes of this invention, any such agent may be included in the construct that is subjected to the method of mitigating the effects of physical aging so long as the conditions of the method will not adversely affect the agent.

This invention has been described in relation to certain examples of its application, in particular to its applicability to constructs comprising semi-crystalline PLA. The examples are not intended nor should they be construed as limiting this invention in any manner whatsoever. Those skilled in the art will recognize, based on the disclosures herein, other polymer and other constructs to which the invention herein may be applied. All such polymers and constructs are within the scope of this invention.

What is claimed:

1. A method of extending the shelf-life of a polymeric construct comprising:
   providing a polymeric construct comprising at least one semi-crystalline polymer;
   determining a glass transition temperature ($T_g$) of each semi-crystalline polymer of the polymeric construct;
   determining a melting temperature ($T_m$) of each semi-crystalline polymer of the polymeric construct;
   heating the polymeric construct to a temperature between $T_g$ and $T_m$ of at least one of the semi-crystalline polymers;
   holding the polymeric construct at the temperature until one or more of the polymers independently is above about 25% crystalline and,
   removing the polymeric construct from the source of heat.

2. The method of claim 1, wherein the temperature is from about $T_g+0.05(T_m-T_g)$ to about $T_g+0.4(T_m-T_g)$.

3. The method of claim 2, wherein the temperature is from about $T_g+0.17(T_m-T_g)$ to about $T_g+0.21(T_m-T_g)$.

4. The method of claim 1, wherein the polymeric construct is held at the temperature until at least one of the semi-crystalline polymers comprising the polymeric construct is from about 40% to about 60% crystalline.

5. The method of claim 1, wherein the polymeric construct is held at the temperature until at least one of the semi-crystalline polymers comprising the polymeric construct is from about 45% to about 55% crystalline.

6. The method of claim 1, wherein one of the semi-crystalline polymers comprising the polymeric construct is poly(lactic acid).

7. The method of claim 6, wherein the polymeric construct is heated at from about 70° C. to about 100° C.

8. The method of claim 7, wherein the polymeric construct is heated at from about 75° C. to about 95° C.

9. The method of claim 8, wherein the polymeric construct is held at from about 75° C. to about 95° C. for from about 5 minutes to about 15 minutes.

10. The method of claim 9, wherein the polymeric construct is held at from about 75° C. to about 95° C. for from about 4 to about 7 minutes.

11. The method of either claim 9 or claim 10, wherein the poly(L-lactic acid) is from about 40% to about 45% crystalline after heating at.

12. The method of claim 1, wherein the construct is a medical device.

13. The method of claim 12, wherein the medical device is an implantable medical device.

14. The method of claim 13, wherein the implantable medical device is a stent.

15. The method of claim 1, wherein the polymeric construct comprises a layer of polymer(s), at least one of which is a semi-crystalline polymer, coated on an implantable medical device.

16. The method of claim 15, wherein one of the semi-crystalline polymers comprising the layer of polymer(s) is poly(lactic acid).

17. The method of claim 16, wherein the implantable medical device is a stent.

18. The method of claim 1, wherein crystallinity is determined by differential scanning calorimetry.

* * * * *